United States Patent [19]

Bender et al.

[11] Patent Number: 5,053,561
[45] Date of Patent: Oct. 1, 1991

[54] METHOD OF ISOLATING TRANS-1,1,4,4-TETRAALKYL-2-BUTENE-1,4-DIOLS

[75] Inventors: Dietmar Bender, Schifferstadt; Klaus Bronstert, Carlsberg; Martin Fischer, Ludwigshafen; Gregor Schuermann, Heidelberg, all of Fed. Rep. of Germany

[73] Assignee: BASF Aktiengesellschaft, Ludwigshafen, Fed. Rep. of Germany

[21] Appl. No.: 537,137

[22] Filed: Jun. 13, 1990

[30] Foreign Application Priority Data

Jun. 13, 1989 [DE] Fed. Rep. of Germany ....... 3919226

[51] Int. Cl.$^5$ .................. C07C 29/86; C07C 33/03; C07C 33/035
[52] U.S. Cl. .................. 568/857; 204/157.9
[58] Field of Search .................. 568/857, 868

[56] References Cited

U.S. PATENT DOCUMENTS

| | | | |
|---|---|---|---|
| 2,081,721 | 5/1937 | van Dijck et al. | 568/868 |
| 2,325,783 | 8/1943 | Lorand | 568/868 |
| 3,053,880 | 9/1962 | Dale | 568/868 |
| 3,304,247 | 2/1967 | Hoffman | 204/158 |
| 3,352,929 | 11/1967 | Hoffman | 260/635 |
| 4,228,094 | 10/1980 | Bryant | 568/868 |
| 4,596,643 | 6/1986 | Hansen | 204/158 R |

FOREIGN PATENT DOCUMENTS

| | | |
|---|---|---|
| 0206756 | 12/1986 | European Pat. Off. |
| 0265053 | 4/1988 | European Pat. Off. |
| 3417943 | 11/1984 | Fed. Rep. of Germany |
| 390061 | 11/1973 | U.S.S.R. ............. 568/857 |
| 1432046 | 10/1988 | U.S.S.R. ............. 568/868 |

OTHER PUBLICATIONS

Beilsteins Handbuch der Organischen Chemie, vol. 1, 260–261 (1928).
Chemical Abstracts, vol. 82, entry 170211 (1975).
Polymer Bull. vol. 19, 427–433 (1988).
Polymer Bull. vol. 18, 433–440 (1987).
Liebigs. Aum. Chem. vol. 608, 195–215 (1957).
J. Org. Chem vol. 29, 1887–1892 (1964).
Helv. Chim. Acta 41, 548–533 (1968).

Primary Examiner—J. E. Evans
Attorney, Agent, or Firm—Keil & Weinkauf

[57] ABSTRACT

A method of isolating trans-1,1,4,4-tetraalkyl-2-butene-1,4-diols of formula I

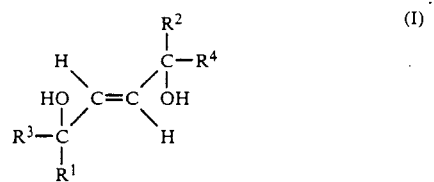

in which $R^1$, $R^2$, $R^3$ and $R^4$ are the same or different and denote $C_1$- to $C_5$-alkyl, from mixtures thereof with their cis-isomers, wherein the trans-isomer is separated from the cis-isomer by liquid-liquid extraction.

7 Claims, No Drawings

METHOD OF ISOLATING TRANS-1,1,4,4-TETRAALKYL-2-BUTENE-1,4-DIOLS

The present invention relates to a method of isolating trans-1,1,4,4-tetraalkyl-2-butene-1,4-diols of formula I

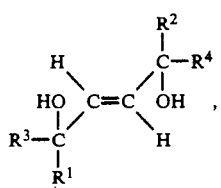

in which $R^1$, $R^2$, $R^3$ and $R^4$ are the same or different and denote $C_1$- to $C_5$-alkyl, from mixtures thereof with their cis-isomers.

The pure trans-diols of formula I and very preferably the trans-diols of formula II below serve as starting compounds for the synthesis of initiator-transfer agents, so-called "inifer initiators", which are initiators for cationic polymerization processes [cf. EP-A 0,265,053; EP-A 0,206,756; *Polymer Bull.* 19, 427 (1988); *Polymer Bull.* 18, 433 (1987)].

The extensive use of such initiators has hitherto been hindered by the expense involved in synthesizing the pure trans-diols I and, in particular, pure trans-2,5-dialkyl-3-hexene-2,5-diol II. Methods of synthesizing these involve either the reduction of 2,5-dimethyl-3-hexyne-2,5-diol with lithium aluminum hydride [*Liebigs Ann. Chem.* 608, 195 (1957)] or the reduction of polymeric peroxides of 2,5-dimethyl-2,4-hexadiene by means of thiolene [*J. Org. Chem.* 29, 1887 (1964)]. Both methods are impracticable and uneconomical on an industrial scale.

In contrast to pure trans-compounds of formula I, mixtures of cis- and trans-1,1,4,4-tetraalkyl-2-butene-1,4-diols can be economically obtained, for example by photochemical or catalytic isomerization of the said cis-isomers [*Helv. Chim. Acta* 51, 548 (1968); DE-A 3,417,943] or by free-radical addition of secondary alcohols to 2-alkyl-3-butyne-2-ols (U.S. Pat. Nos. 3,304,247; 3,352,929). The cis-isomers required for photochemical isomerization can be obtained in very good yields by the catalytic reduction of trans-1,1,4,4-tetraalkyl-2-butyne-1,4-diols with hydrogen [cf. *J. Org. Chem.* 29, 1887 (1964)]. However, due to the great structural similarity between the cis- and trans-compounds and to their very similar physical properties, a method of economically isolating trans-1,1-4-4-tetraalkyl-2-butene-1,4-diols and in particular trans-2,5-dialkyl-3-hexene-2,5-diols from mixtures thereof with the cis-isomers on an industrial scale has not hitherto been known. It is our object, therefore, to provide such a method.

Accordingly, we have found a method of isolating trans-1,1,4,4-tetraalkyl-2-butene-1,4-diols of formula I

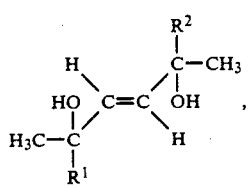

in which $R^1$, $R^2$, $R^3$ and $R^4$ are the same or different and denote $C_1$- to $C_5$-alkyl, from mixtures thereof with their cis-isomers, wherein the trans-isomers are separated from the cis-isomers by liquid-liquid extraction.

The method of the invention is suitable for the isolation of trans-alkenediols of formula I, in which $R^1$, $R^2$, $R^3$ and $R^4$ are the same or different and denote $C_1$- to $C_5$-alkyl, from mixtures thereof with their cis-isomers. The method of the invention is preferably used for isolating trans-alkenediols I, in which $R^3$ and $R^4$ are each methyl, i.e. for isolating trans-2,5-dialkyl-3-hexene-2,5-diols of the general formula II

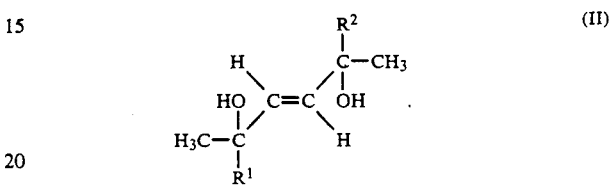

The method of the invention is particularly preferably used for the isolation of trans-alkenediols II, in which $R^1$ and $R^2$ are the same, and very preferably for the isolation of trans-2,5-dimethyl-3-hexene-2,5-diol.

The liquid-liquid extraction process used in the present invention may be carried out continuously or batchwise in conventional liquid-liquid extractors such as are described, for example, in *Ullmanns Encyklopädie der techn. Chemie*, Vol. 2, pp. 560–565, 4th Edition, Verlag Chemie, Weinheim, 1972. Extraction is effected using a polar and a non-polar phase, in which case the cis- and trans-isomers accumulate to varying extents in the different phases such that selective separation of the trans-isomer is possible.

The polar phase used may be water or a mixture of water and other polar solvents showing a good degree of solubility in water, for example cyclic ureas, dimethyl formamide, tetrahydrofuran, methoxy ethanol, dimethyl sulfoxide, hexamethylphosphoric triamide, acetone and lower alcohols, particularly methanol and ethanol. When using water/solvent mixtures, however, care should be taken to ensure that such mixtures do not form an emulsion with the non-polar phase, and this should be checked by pretesting if necessary. The preferred polar phase is water or a mixture of water and a $C_1$–$C_4$-alcohol, especially methanol and/or ethanol. The use of solutions of higher alcohols in water, as the polar phase, is also possible and is equivalent to the use of $C_1$–$C_4$-alcohol/water mixtures. However, due to their moderate degree of solubility in water, the use of such higher alcohols provides no added advantage over the use of lower alcohols.

The non-polar phase preferably comprises aliphatic, alkylaromatic or aromatic hydrocarbons or mixtures of these solvents. Good results may also be achieved by using, as non-polar phase, halogenated aliphatic or aromatic hydrocarbons or long-chain, i.e. higher than $C_5$-ketones either alone or in admixture with the aforementioned non-polar solvents.

Obviously, the solvents used as extracting agents must be chemically inert to the alkenediol I. For phase separation to take place, it is necessary that the polar and non-polar phases vary in density, the speed at which phase separation occurs being greater, the greater the disparity in density of the phases.

To achieve separation of the cis- and trans-isomers of the alkenediols I which is as complete, efficient and economical as possible, it is necessary, when selecting the solvents for the polar and non-polar phases, to ensure that the quotient of the distribution coefficients $k_{trans}/k_{cis}$ of the trans- and cis-isomers between the polar and non-polar phases is as large as possible. The distribution coefficient k of the cis- or trans-isomer is defined as the concentration of isomer in the polar phase divided by the concentration of the same isomer in the non-polar phase in the equilibrium state, as illustrated by the following equations (1) and (2):

$$k_{cis} = \frac{\text{concentration of cis-isomer in polar phase}}{\text{concentration of cis-isomer in non-polar phase}} \quad (1)$$

$$k_{trans} = \frac{\text{concentration of trans-isomer in polar phase}}{\text{concentration of trans-isomer in non-polar phase}} \quad (2)$$

Table 1 below shows, by way of example, the distribution coefficients k as determined for cis- and trans-2,5-dimethyl-3-hexene-2,5-diol between various polar and non-polar phases. It is seen from said distribution coefficients that the cis-isomer of 2,5-dimethyl-3-hexene-2,5-diol accumulates in the non-polar phase, whilst its trans-isomer accumulates in the polar phase. All of the solvents and solvent mixtures given in Table 1 are suitable for the process of the invention.

The extraction process of the invention is generally carried out at atmospheric pressure or under the autogenic pressure of the extracting agents, at temperatures ranging from 0° to 100° C., preferably from 15° to 85° C. The temperature used for extraction will generally be chosen so as to be below the boiling point of one of the solvents used. If this temperature is above the boiling point of one of the extracting agents used, it will often be advantageous to effect extraction under the autogenous pressure of the extracting agents or under exogenously elevated pressure.

The extracting agents used to separate the cis-/trans-alkenediol mixture are conveniently employed in amounts such that one or other of the trans- and cis-isomers can be completely dissolved by one or other of the polar and non-polar phases. Larger amounts may be advantageous, but it should be remembered that the extracting agents used for isolating the cis- and trans-isomers must be subsequently removed by distillation.

The ratio of polar to non-polar phase, by volume, may also be varied over a wide range and is generally from 0.1:1 to 10:1 and preferably from 0.8:1 to 3:1.

In practice, the process is carried out by dissolving the cis-/trans-isomer mixture, such as is obtained from the addition of secondary alcohols to 2-alkyl-3-butyne-2-ols, in the two-phase mixture of extracting agents. This dissolution causes a large portion of the cis-alkenediol to pass into the non-polar phase, which may then be removed. The polar phase, which still contains both isomers, may then be extracted with the solvent used for the non-polar phase, for example in a countercurrent extractor. Following this treatment, the polar phase may be evaporated off, if necessary under reduced pressure, the residue being concentrated by evaporation to give the trans-isomer in virtually pure form. Advantageously, the combined non-polar phases containing accumulations of cis-isomer may be re-extracted with the solvent used for the polar phase so that they eventually contain only slight amounts of trans-isomer. The cis-alkenediol now present virtually exclusively in the non-polar phase is then isomerized, preferably photochemically, and the non-polar phase, which now contains a mixture of cis- and trans-isomers, is either recycled to the first extraction stage or, prior thereto, extracted a number of times or, preferably, once, with the solvent used for the polar phase. Photochemical isomerization of the cis-alkenediol may then take place in conventional manner, for example by the method described in DE-A 3,417,943. In this way, the cis-/trans-isomer mixture of 2,5-dialkyl-3-hexene-2,5-diols can be gradually converted, virtually quantitatively, to pure trans-isomer, which is isolated as such in good yields.

EXAMPLES

2,5-Dimethyl-3-hexene-2,5-diol 2,5-Dimethyl-3-hexene-2,5-diol was prepared by free-radical addition of isopropanol to 2-methyl-3-butyne-2-ol by the method of U.S. Pat. No. 3,352,929.

Determination of the Distribution Coefficients for cis- and trans-2,5-dimethyl-3-hexene-2,5-diol 2 g of cis- or trans-alkenediol were dissolved, at 25° C., in a mixture of 40 ml of a polar solvent and 40 ml of a non-polar solvent. The mixture was vigorously shaken in a separating funnel for 10 minutes. Following separation of the phases, the solvents were removed by distillation under reduced pressure. The residues were weighed, and the results were used to calculate the distribution coefficients as defined in equations (1) and (2) above (see Table 1 below).

TABLE 1

| 2,5-Diol | Distribution coefficients of cis- and trans-2,5-dimethyl-3-hexene-2,5-diol | | |
|---|---|---|---|
| | Polar phase | Non-polar phase | k |
| cis | water | methyl cyclohexane | 0.61 |
| cis | water | cyclohexane | 0.56 |
| cis | water | n-hexane | 0.76 |
| cis | water | toluene | 0.38 |
| cis | water | methylene chloride | 0.17 |
| cis | water | methyl isobutylketone | 0.09 |
| cis | water + 2% methanol | toluene | 0.39 |
| cis | water + 10% ethanol | toluene | 0.35 |
| trans | water | methyl cyclohexane | 52 |
| trans | water | cyclohexane | 30 |
| trans | water | n-hexane | 34 |
| trans | water | toluene | 25 |
| trans | water | methylene chloride | 7.3 |
| trans | water | methyl isobutylketone | 3.0 |
| trans | water + 2% methanol | toluene | 62 |
| trans | water + 10% ethanol | toluene | 23 |

Photochemical Isomerization of cis-2,5-dimethyl-3-hexene-2,5-diol 120 g of cis-2,5-dimethyl-3-hexene-2,5-diol were mixed with 1,2 g of diphenyl sulfide in a light-exposure apparatus having a capacity of 200 ml. This mixture was exposed to the light of a 300 W high-pressure mercury lamp for 48 hours at a temperature of 90° C. After 10 hours the cis:trans ratio was 46:54, and after 48 hours it was 22:78, as determined by NMR spectroscopy and gas chromatography.

Isolation of trans-2,5-dimethyl-3-hexene-2,5-diol from a Mixture of its cis- and trans-isomers 25 kg of a mixture of 30% cis- and 70% trans-2,5-dimethyl-3-hexene-2,5-diol were dissolved in a mixture of 100 l of water and 10 l of toluene. The organic phase, in which half of the cis-alkenediol accumulated during dissolution, was separated off. The aqueous phase was extracted at 50° C. with toluene in a liquid-liquid counter-current extractor comprising a sieve tray column (30 sieve trays, column diameter 50 cm, column packed to a height of 100 cm) and a pulsating pump (throughput rates: 3 l/h of aqueous solution, 2 l/h of toluene). Following concentration of the aqueous phase by evaporation, there were obtained 8.5 kg of trans-2,5-dimethyl-3-hexene-2,5-diol having a purity of 99%. The combined toluene phases were again extracted with 100 l of water under the above conditions. A mixture of 95% of cis-isomer and 5% of trans-isomer remained in the toluene phase, whilst the trans-isomer accumulated in the aqueous phase to an extent of approx. 85%. The aqueous phase was re-extracted with toluene and then concentrated to give, as residue, 7 kg of trans-isomer having a purity of 98.5%. Based on the initial weight of the cis-/trans-alkenediol, the yield of pure trans-isomer was more than 88%. The cis-isomer which had accumulated in the organic phase was separated from solvent and partially converted photochemically to the trans-isomer, and the resulting cis-/trans-isomer mixture was recycled to the extraction circuit.

We claim:

1. A method of isolating trans-1,1,4,4-tetraalkyl-2-butene-1,4-diols of formula I

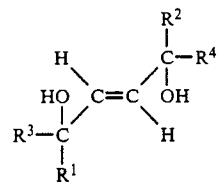

in which $R^1$, $R^2$, $R^3$ and $R^4$ are the same or different and denote $C_1$- to $C_5$-alkyl, from mixtures thereof with their cis-isomers, wherein the trans-isomer is separated from the cis-isomer by liquid-liquid extraction.

2. A method as claimed in claim 1, wherein trans-2,5-dialkyl-3-hexene-2,5-diols of formula II

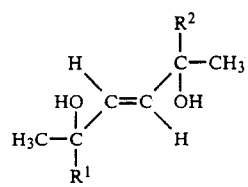

are isolated from mixtures thereof with the respective cis-isomers by liquid-liquid extraction.

3. A method as claimed in claim 1, wherein the cis-isomer is removed with the non-polar phase.

4. A method as claimed in claim 1, wherein the polar phase used is water or a mixture of water and $C_1$-$C_4$-alcohols.

5. A method as claimed in claim 1, wherein the polar phase used is water or a mixture of water with methanol and/or ethanol.

6. A method as claimed in claim 1, wherein the trans-isomer is separated from the cis-isomer by liquid-liquid extraction, whereupon the cis-isomer is isomerized to a mixture of cis- and trans-isomers, from which the trans-isomer is again isolated by liquid-liquid extraction.

7. A method as claimed in claim 6, wherein said isomerization is effected photochemically.

* * * * *